United States Patent [19]

Coe et al.

[11] Patent Number: 4,931,039
[45] Date of Patent: Jun. 5, 1990

[54] VENTRICULAR CATHETER INTRODUCER

[75] Inventors: Frederick L. Coe, Santa Barbara, Calif.; Michael E. Lachman, Deerfield, Ill.

[73] Assignee: Baxter International Inc., Deerfield, Ill.

[21] Appl. No.: 261,048

[22] Filed: Oct. 21, 1988

[51] Int. Cl.$^5$ ............................................. A61M 31/00
[52] U.S. Cl. ............................................. 604/53; 604/9; 604/164; 604/264; 604/170
[58] Field of Search ............ 604/53, 164, 264, 8, 604/9, 93, 170, 43, 95, 280, 270; 128/207.14, 207.15, 200.26

[56] References Cited

U.S. PATENT DOCUMENTS

| | | | |
|---|---|---|---|
| 2,393,002 | 1/1946 | Smith | 604/43 |
| 2,460,473 | 2/1949 | Smith | 604/43 |
| 2,717,600 | 9/1955 | Huber | 604/164 X |
| 3,618,613 | 11/1971 | Schulte | . |
| 3,769,982 | 11/1973 | Schulte | . |
| 4,364,395 | 12/1982 | Redmond et al. | . |
| 4,518,383 | 5/1985 | Evans | 604/164 X |
| 4,613,324 | 9/1986 | Ghajar | 604/264 X |
| 4,781,691 | 11/1988 | Gross | 604/164 |
| 4,784,638 | 11/1988 | Ghajar et al. | 604/9 X |
| 4,790,817 | 12/1988 | Luther | 604/264 X |

Primary Examiner—Richard J. Apley
Assistant Examiner—J. L. Doyle
Attorney, Agent, or Firm—Paul C. Flattery; Bradford R. L. Price; Robert E. Hartenberger

[57] ABSTRACT

An external introducer for a ventricular catheter that is part of a hydrocephalus shunt system. The introducer includes a stylet assembly that mates with a cannula assembly. The cannula assembly comprises a cannula having a bent tip and an opening on the sidewall of the cannula, and a cannula hub into which a catheter is clipped. The stylet assembly includes a flexible stylet attached to a stylet hub. When the stylet hub is locked to the cannula hub, the stylet protrudes slightly from the end of the cannula at an angle. The introducer holds the catheter approximately straight for insertion into the ventricle of the brain.

21 Claims, 3 Drawing Sheets

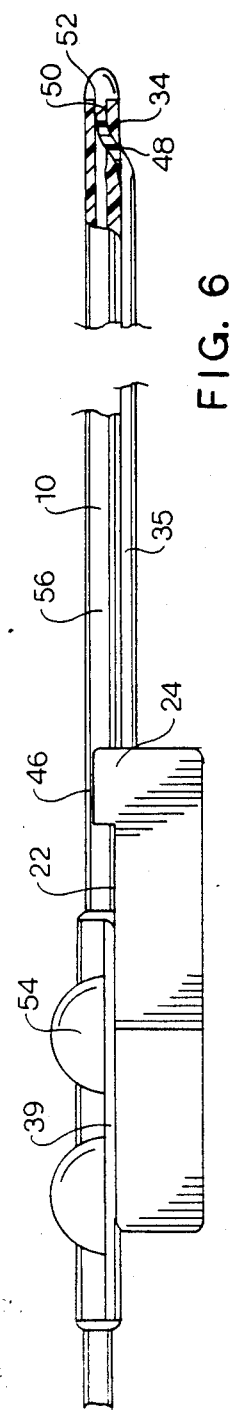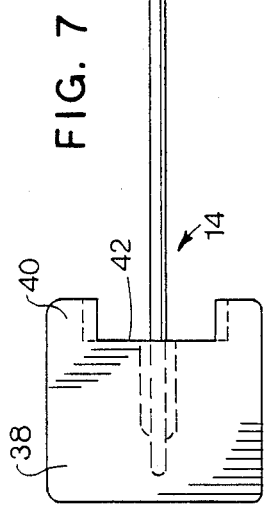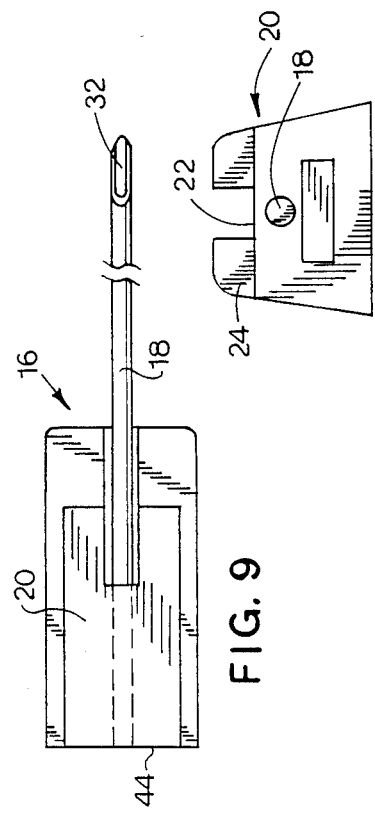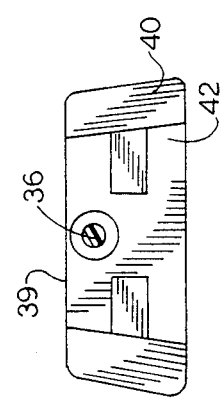

VENTRICULAR CATHETER INTRODUCER

BACKGROUND OF THE INVENTION

This invention relates to an apparatus for inserting a catheter into the ventricles of the brain.

Shunt systems are required in the treatment of hydrocephalus for draining excess cerebrospinal fluid from the ventricles of the brain either to the right atrium of the heart or to the peritoneum. One such shunt system is described in two recent patents, both entitled "Low Profile Shunt System," U.S. Pat. Nos. 4,364,395 issued Dec. 21, 1982 and 4,464,168 issued Aug. 7, 1984. Both patents are assigned to the same assignee as the present invention and are herein incorporated by reference.

One component of a hydrocephalus shunt system, the ventricular catheter, must be inserted through a hole in the skull and through brain tissue so that the tip of the catheter lies in the ventricle of the brain. The ventricular catheter is made from a soft silicone material and must be supported in order to ensure proper insertion into the brain tissue. If the ventricular catheter is supplied as a separate component of the shunt system, an internal stylet may be inserted into the open end of the catheter to provide support during insertion. However a shunt system which consists of separate components (ventricular catheter, valve, and atrial or peritoneal catheter) is more difficult to implant because it requires connecting the separate components during the surgical procedure.

A one piece shunt system is also available which includes all of the components discussed above. However, this design has no open end for insertion of the supporting internal stylet into the ventricular catheter. One method of inserting a one piece shunt system into the ventricle is to first insert into the brain a rigid rod of approximately the same as or slightly larger diameter than the catheter. The rod is then removed and the catheter is quickly pushed through the path created by the rod. One of the problems associated with this method is that it is still difficult to push the catheter into the proper position in the ventricle because the catheter is unsupported when it is inserted.

Another method of inserting the one piece shunt ventricular catheter is to use an external introducer. External introducers generally consist of a stylet which passes through and protrudes from a cannula. The tip of the stylet is inserted through one of the proximal drainage holes in the catheter in order to internally support the catheter tip during insertion into the brain. The cannula is positioned adjacent the length of the catheter. After insertion of the introducer and catheter into the brain, the stylet is retracted, releasing the tip of the catheter. The cannula is then retracted from the brain.

The problem with the introducers presently available is that the introducer and catheter assembly has a relatively large profile in cross-section. In these assemblies, the catheter tip is held at an angle with respect to the rest of the catheter and there is also a space between the distal portion of the catheter and the cannula. Thus the cross-sectional profile of the connected introducer and catheter is larger than the sum of their individual profiles, causing unnecessary displacement of brain tissue. It is desirable to minimize the cross-sectional profile of the introducer and catheter assembly to reduce the trauma to the brain caused by brain tissue being displaced during the insertion of the assembly.

SUMMARY OF THE INVENTION

The present invention provides a lower profile introducer/catheter assembly while providing excellent external support for insertion of the catheter. The introducer includes a rigid cannula attached to a cannula hub and a flexible stylet attached to a stylet hub. The cannula has a bent tip with an opening on the side so that the end portion of the stylet protrudes from the cannula at an angle when the stylet is fully inserted into the cannula. When assembled, the cannula and catheter are in contact substantially along their inserted length and the catheter tip is not deflected significantly.

The end portion of the stylet is then inserted into the most proximal drainage hole of the ventricular catheter and a more distal portion of the catheter is clipped into a slot in the cannula hub. After the catheter is inserted into the ventricle, the distal portion of the catheter is unclipped from the cannula hub, and the stylet is retracted from the cannula. The cannula is then removed, leaving the catheter implanted in the brain.

A BRIEF DESCRIPTION OF THE DRAWINGS

FIG. 6 is a side view of the introducer and catheter showing a partial section of the catheter.

FIG. 7 is a top view of the stylet assembly.

FIG. 8 is an end view of the stylet assembly.

FIG. 9 is a top view of the cannula assembly.

FIG. 10 is an end view of the cannula.

DETAILED DESCRIPTION OF THE INVENTION

Figure 1:
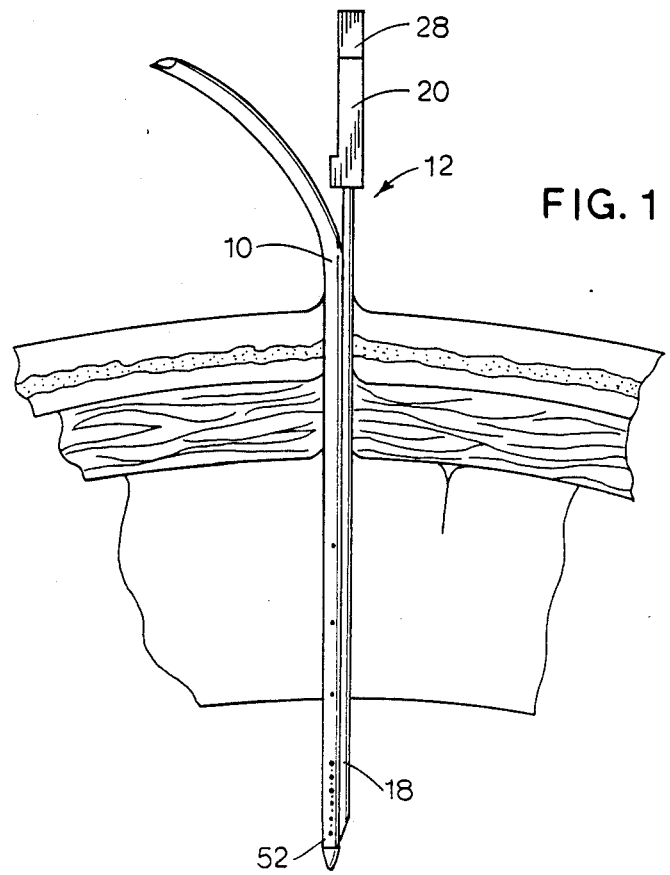
FIG. 1 is a schematic view of the introducer and catheter inserted into the ventricle of the brain.
Figure 11:
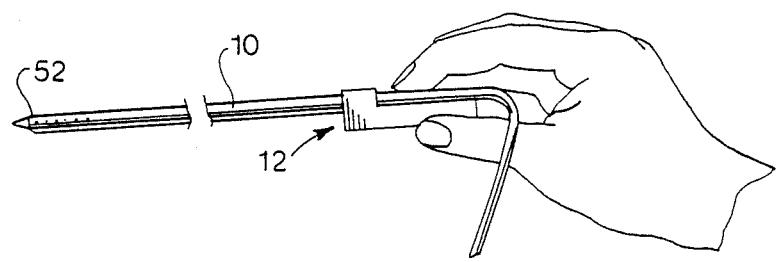
FIG. 11 is a perspective view of the introducer being used.
Figure 2:
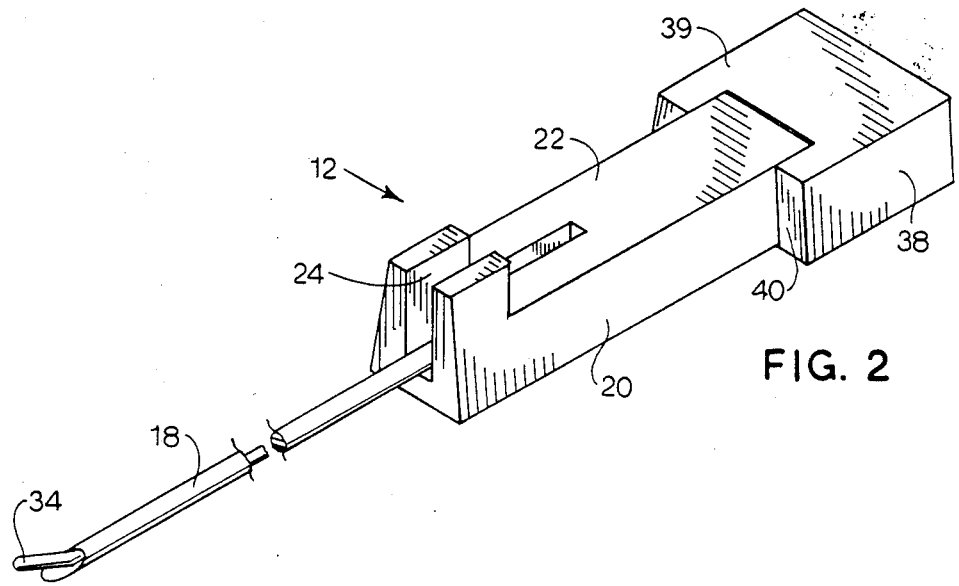
FIG. 2 is a perspective view of the introducer.
Figure 3:
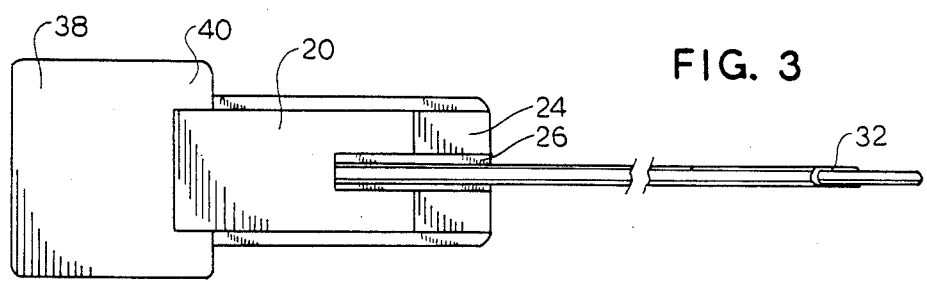
FIG. 3 is a top view of the introducer.
Figure 4:
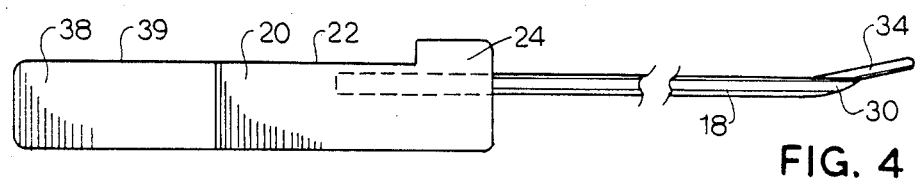
FIG. 4 is a side view of the introducer.
Figure 5:
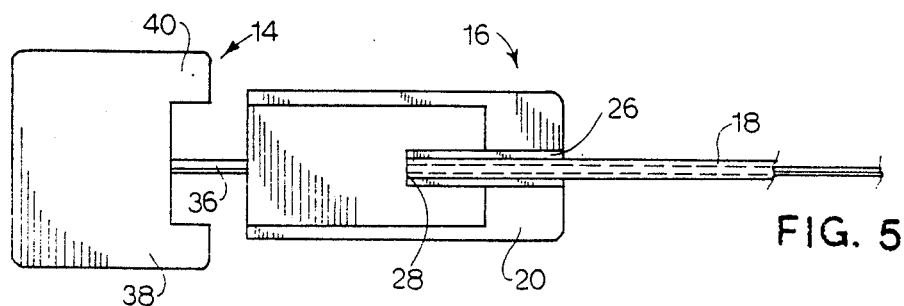
FIG. 5 is a top view of the introducer with the stylet retracted.

With reference to FIG. 1 there is shown a ventricular catheter 10 and external introducer, generally identified as 12. The introducer 12 is shown in more detail in FIG. 3. The introducer 12 comprises of a stylet assembly 14 and cannula assembly 16 as shown in FIGS. 7-10.

The cannula assembly includes a cannula 18, often described as a "tuohy needle". The cannula 18 is securely mounted to a cannula hub 20. A cannula length of ten cm. extending from the hub is generally sufficient for most uses. The cannula hub 20 has the approximate shape of a trapezoidal prism as shown in FIG. 10. Cannula hub 20 also includes two nubs 24 spaced apart a distance slightly less than the diameter of a catheter. As will be described later, the catheter is placed between these two nubs to clip the catheter in place prior to insertion of the catheter and introducer into the ventricle. This arrangement acts as a type of clipping means. Cannula hub 20 also includes a slot 26 that extends between the nubs 24 and for a distance beyond on the top of hub 20. There is a space between the cannula 18 and all walls of the slot 26, except that cannula 18 is secured to the back wall 28 of slot 26 and passes through the entire length of cannula hub 20.

The cannula 18 is straight with a bent tip 30 at the open end. The tip is bent and ground so that opening 32 is on the side of the cannula, approximately co-extensive with the sidewall of the cannula 18.

The stylet assembly 14 comprises a stylet 36 secured to a stylet hub 38. The stylet 36 is formed of a flexible material, such as nylon. The stylet hub 38 has the approximate shape of a trapezoidal prism. The stylet hub 38 has two arms 40 which form a trapezoidal shaped recess 42 which mates with the end 44 of the cannula hub. When the stylet is in the fully inserted position within the cannula, the cannula hub 20 fits securely within the recess 42 and because of the trapezoidal shape of the cannula hub 20 and the recess, the two components will not twist or turn with respect to each other. The hub design described herein is one of many possible configurations which allows the catheter to be held tightly against the cannula, the stylet hub to mate with the cannula hub, and the introducer to be easily handled by the user.

The trapezoidal shape of the hubs allows the user to quickly identify the correct alignment of the hubs in connecting them together. The cross-sectional shape prevents the user from locking the cannula hub 20 and the stylet hub 38 together with an improper alignment.

To assemble the introducer, the end portion 34 of the stylet 36 is inserted into the cannula 18 at the end 44 of the cannula hub 20. When the cannula hub 20 is fitted into the recess 42 of the stylet hub, the length of the stylet is such that the end portion 34 protrudes from the cannula 18 a distance sufficient to properly support a ventricular catheter tip. When the catheter and introducer assembly is in the first position as shown in FIG. 6, the stylet end portion 34 extends through the cannula opening 32 and is positioned within the catheter tip 52. By way of an example, the end portion 34 protruding from the cannula opening 32 may be approximately ⅛ inch at an angle of 12°±2° to the main portion 35 of the stylet 36 and to the longitudinal axis of the cannula 18. However, it is believed that an angle in the range of about 5 degrees to about 20 degrees may also work with the present invention. FIG. 6 shows the introducer inserted into a catheter.

Because the stylet end portion 34 protrudes from the cannula opening 32 at an angle, the catheter tip 52 is held substantially straight with respect to the main portion 56 of the catheter. This contrasts with the prior art introducers which may include a cannula with a stylet protruding from the end of the cannula. This causes the catheter tip to be held at an angle with respect to the remainder of the catheter. With these prior designs, the catheter twitches when the stylet is retracted as will be described later.

In some embodiments of the present invention, the longitudinal axis of the catheter tip is parallel to, but not coextensive with the longitudinal axis of the remainder of the catheter. The resulting cross section of the catheter and introducer assembly is still less than that of the prior art catheters and introducers, and the movement of the catheter tip upon retraction of the stylet is also greatly reduced.

The catheter and the cannula are positioned approximately parallel to and in contact with one another. This provides an extremely low profile for the catheter and external introducer assembly. To further reduce the profile of the assembly the catheter may be stretched slightly before clipping a distal portion 46 between the nubs 24 of the cannula hub 20 so that the catheter is held in tension. It is important to minimize the profile of the catheter/introducer assembly so that the amount of brain tissue displaced is minimized.

Cannula 18 and stylet 36 are both positioned adjacent the top surfaces, 22 and 39, respectively, of the cannula hub 20 and stylet hub 38. The cannula hub top surface 22 is coplanar with the stylet hub top surface 39 to provide a flat surface for the catheter valve 54. This arrangement helps position the catheter 10 flat against the cannula 18 and against the hubs 20 and 38, past the locking nubs 24, so that a reservoir in line with the catheter can lay flat on top surfaces 22 and 39. This feature makes the catheter/introducer assembly easier to handle during insertion of the catheter.

As shown in FIG. 6 the end portion 34 of the stylet is inserted in the most proximal drainage hole 48 of the catheter. The distance between the most proximal drainage hole 48 and the inside surface 50 of the catheter tip 52 must be appropriate to accept the end portion 34 of the stylet 36 protruding from the cannula 18.

The introducer is removed from the patient by first unclipping the catheter to release the tension in the catheter. The stylet hub 38 is then retracted from the cannula hub 20 thereby retracting the stylet from the interior of the catheter and the drainage hole 48. It is preferred that the end portion 34 of the stylet be moved so that it is positioned completely within the cannula 18. This releases the end of the catheter in the ventricle. Because the introducer holds the catheter tip 52 approximately straight with respect to the rest of the catheter 10, the catheter tip 52 remains rather still when the stylet is retracted.

A problem occurs with other external introducers which hold the catheter tip at an angle. These other introducers cause the catheter tip to displace suddenly when the stylet is retracted. This sudden movement could be traumatic to the patient and is best avoided. The present invention solves that problem by holding the catheter tip approximately straight. When the stylet is retracted, the catheter does not twitch significantly.

While the invention has particularly been shown and described with reference to a preferred embodiment, it will be understood by those skilled in the art that variation in form, construction and arrangement may be made therein without departing from the spirit and scope of the invention.

We claim:

1. An introducer for a catheter, the catheter being flexible and comprising a main portion, a proximal tip and a hole adjacent the proximal tip, the introducer comprising:
   a cannula having a tip, a sidewall and an opening in the sidewall adjacent the tip;
   supporting means for supporting the catheter tip, the supporting means comprising a flexible stylet having an end portion, whereupon the stylet being in a first position within the cannula, the end portion of the stylet is adapted to extend through the cannula sidewall opening and into the catheter hole.

2. The introducer as claimed in claim 1, wherein the cannula tip is bent.

3. An introducer for a catheter, the catheter being flexible and comprising a main portion, a proximal tip and a hole adjacent the proximal tip, the introducer comprising:
   a cannula having a tip, a sidewall and an opening in the sidewall adjacent the tip;
   supporting means for supporting the catheter tip, the supporting means comprising a flexible stylet having an end portion, whereupon the stylet being in a first position within the cannula, the end portion of the stylet is adapted to extend through the cannula sidewall opening and into the catheter hole;

wherein the main portion of the catheter and the proximal tip of the catheter each comprise a longitudinal axis, the longitudinal axes of the main portion and proximal tip being coaxial when the catheter is not assembled with the introducer, when the catheter and the introducer are in a first position the stylet supports the catheter in a manner such that the longitudinal axis of the proximal tip is substantially parallel to the longitudinal axis of the catheter main portion.

4. The introducer as claimed in calim 1, the introducer also comprising a cannula hub, a portion of the cannula projecting forwardly from the cannula hub, wherein upon the introducer and the catheter being in a first position the catheter engages the cannula along a substantial length of the cannula projecting forwardly from the cannula hub.

5. An introducer for a catheter, the catheter being flexible and comprising a main portion, a proximal tip and a hole adjacent the proximal tip, the introducer comprising:
  a cannula having a tip, a sidewall and an opening in the sidewall adjacent the tip;
  supporting means for supporting the catheter tip, the supporting means comprising a flexible stylet having an end portion, whereupon the stylet being in a first position within the cannula, the end portion of the stylet is adapted to extend through the cannula sidewall opening and into the catheter hole;
  a cannula hub, a portion of the cannula projecting forwardly from the cannula hub, wherein upon the introducer and the catheter being in a first position the catheter engages the cannula along a substantial length of the cannula projecting forwardly from the cannula hub, the cannula hub also comprising clipping means adapted to clip a portion of the catheter to the cannula hub.

6. The introducer as claimed in claim 4, the introducer also comprising a stylet hub, the stylet projecting forwardly from the stylet hub, wherein the stylet being in the first position, the stylet hub mates with the cannula hub and the stylet hub and the cannula hub cannot be rotated with respect to one another.

7. The introducer as claimed in claim 4, the introducer also comprising a stylet hub connected to the stylet, the stylet hub and the cannula hub each comprising a top surface, wherein upon the stylet being in the first position, the top surfaces of the stylet hub and cannula hub are coplanar.

8. An introducer as claimed in claim 5, wherein the clipping means comprises a pair of nubs spaced a predetermined distance apart.

9. An introducer as claimed in claim 8, wherein the cannula hub additionally comprises a slot between the pair of nubs.

10. An introducer for a catheter, the catheter being flexible and comprising a main portion, a proximal tip and a hole adjacent the proximal tip, the introducer comprising:
  a cannula having a tip, a sidewall and an opening in the sidewall adjacent the tip;
  supporting means for supporting the catheter tip, the supporting means comprising a flexible stylet having an end portion, the stylet having an inserted position within the cannula, whereupon the stylet being in the fully inserted position within the cannula, the end portion of the stylet is adapted to extend through the cannula opening and into the catheter hole and the end portion of the stylet forms an angle with the main portion of the stylet.

11. An introducer as claimed in claim 10, wherein the angle between the end portion of the stylet and the main portion of the stylet is in the range of about 5 degrees to about 20 degrees.

12. A catheter and introducer assembly comprising:
  a flexible catheter comprising a main portion, a proximal tip and a proximal hole adjacent the proximal tip,
  a cannula comprising a bent tip, a sidewall, and an opening adjacent the tip, and
  a stylet comprising an end portion and a main portion, the stylet being adapted for positioning within the cannula, the stylet having a first position wherein the stylet end portion protrudes through the cannula opening and is positioned within the catheter proximal tip, the stylet end portion forming an angle with the stylet main portion, wherein the catheter tip is held in a substantially straight position with respect to the main portion of the catheter.

13. A catheter and introducer assembly as claimed in claim 12, wherein the assembly comprises a predetermined insertion length adapted for insertion into a patient's body, upon the catheter and introducer being in the first position, the catheter engages the introducer along substantially the entire predetermined insertion length prior to the assembly being inserted into the patient's body.

14. A catheter and introducer assembly as claimed in claim 12, additionally comprising a cannula hub, wherein the cannula is connected to the cannula hub and the catheter engages the cannula adjacent the cannula hub.

15. A catheter and introducer assembly as claimed in claim 14, the cannula hub additionally comprising clipping means, wherein upon a portion of the catheter being clipped to the cannula hub by the clipping means, the catheter engages the cannula adjacent the clipping means.

16. A catheter and introducer assembly as claimed in claim 15, wherein the cannula hub comprises a slot adjacent the clipping means wherein a portion of the catheter is placed a least partially within the slot to engage the cannula.

17. A catheter and introducer assembly comprising:
  a flexible catheter comprising a main portion, a proximal tip and a proximal hole adjacent the proximal tip,
  a cannula comprising a bent tip, a sidewall, and an opening in the sidewall adjacent the tip, and
  a stylet comprising an end portion and a main portion, the stylet being adapted for positioning within the cannula, the stylet having a first position wherein the stylet end portion protrudes through the cannula opening and is positioned within the catheter proximal tip, wherein the stylet end portion forms an angle of less than 180 degrees with the stylet main portion, wherein the catheter tip is held in a substantially straight position with respect to the main portion of the catheter.

18. An introducer for a catheter, the catheter being flexible and comprising a main portion, a proximal tip and a hole adjacent the proximal tip, the introducer comprising:

a cannula having a tip, a sidewall and an opening in the sidewall adjacent the tip;

supporting means for supporting the catheter tip, the supporting means comprising a flexible stylet having a main portion and an end portion, whereupon the stylet being in a first position within the cannula, the stylet main portion is adapted to extend substantially parallel to the catheter main portion and the stylet end portion is adapted to extend through the cannula sidewall opening and into the catheter hole.

19. The introducer as claimed in claim 18, wherein the cannula tip is bent.

20. An introducer for a catheter, the catheter being flexible and comprising a main portion, a proximal tip and a hole adjacent the proximal tip, the introducer comprising:

a cannula having a tip, a sidewall and an opening in the sidewall adjacent the tip;

supporting means for supporting the catheter tip, the supporting means comprising a flexible stylet having a main portion and an end portion, whereupon the stylet being in a first position within the cannula, the stylet main portion is adapted to extend substantially parallel to but not positioned within the catheter main portion and the stylet end portion is adapted to extend through the cannula sidewall opening and into the catheter hole.

21. The introducer as claimed in claim 20, wherein the cannula tip is bent.

* * * * *